United States Patent [19]

Radzins

[11] 4,364,787
[45] Dec. 21, 1982

[54] APPARATUS FOR APPLYING ELASTIC RIBBON SEGMENTS TO DIAPERS

[75] Inventor: Edmund Radzins, Sheboygan Falls, Wis.

[73] Assignee: Curt G. Joa, Inc., Sheboygan Falls, Wis.

[21] Appl. No.: 295,338

[22] Filed: Aug. 24, 1981

Related U.S. Application Data

[63] Continuation of Ser. No. 180,256, Aug. 22, 1980, abandoned.

[51] Int. Cl.³ .............................................. B32B 31/08
[52] U.S. Cl. .................................. 156/164; 156/229; 156/265; 156/269; 156/302; 156/495; 156/519; 156/522; 156/549; 156/552; 156/578
[58] Field of Search ............... 156/163, 164, 229, 265, 156/269, 299, 302, 303, 494, 495, 519, 521, 522, 549, 552, 578; 271/276, 277, 196

[56] References Cited

U.S. PATENT DOCUMENTS

| | | | |
|---|---|---|---|
| 1,823,876 | 9/1931 | Broadmeyer | 156/521 |
| 3,096,088 | 7/1963 | Young | 271/277 |
| 3,159,521 | 12/1964 | Pechmann | 156/519 |
| 3,898,117 | 8/1975 | Taylor | 156/265 |
| 3,957,570 | 5/1976 | Helm | 156/521 |
| 4,024,814 | 5/1977 | Becker | 271/276 |
| 4,061,521 | 12/1977 | Lerner et al. | 156/265 |
| 4,227,952 | 10/1980 | Sabee | 156/164 |
| 4,239,578 | 12/1980 | Gore | 156/164 |
| 4,261,782 | 4/1981 | Teed | 156/164 |
| 4,284,454 | 8/1981 | Joa | 156/163 |
| 4,285,747 | 8/1981 | Rega | 156/164 |
| 4,293,367 | 10/1981 | Klasek et al. | 156/164 |
| 4,297,157 | 6/1980 | Van Vliet | 156/164 |
| 4,300,967 | 11/1981 | Sigl | 156/164 |

Primary Examiner—Jerome W. Massie
Attorney, Agent, or Firm—Ralph G. Hohenfeldt

[57] ABSTRACT

To make diapers having elasticized regions, unstretched segments of elastic ribbon are deposited on a first rotating roll which has vacuum holes in its periphery for attracting the body of a segment and a mechanical element for temporarily securing one end. The first roll rotates segments successively to a place adjacent a second roll which has a larger radius and, hence, higher peripheral velocity than the first roll. The second roll has grippers spaced apart by an amount substantially equal to the desired stretched length of the segments. The leading end of each segment on the first roll is engaged by a gripper on the second higher speed roll so the segment stretches after which a lifter on the first roll releases the trailing end for it to be engaged by a gripper to hold the stretched segment on the second roll. Quick setting glue is applied to the stretched segments and the top porous sheet material comprising the diaper is run in contact with the segments to pick them up. The exposed faces of the segments have glue applied and the sheet is superposed on a moving non-porous backing sheet on which absorbent pads have been deposited and a continuous diaper web is formed. The web is cut transversely and remotely from the segments and individual diapers are formed.

9 Claims, 7 Drawing Figures

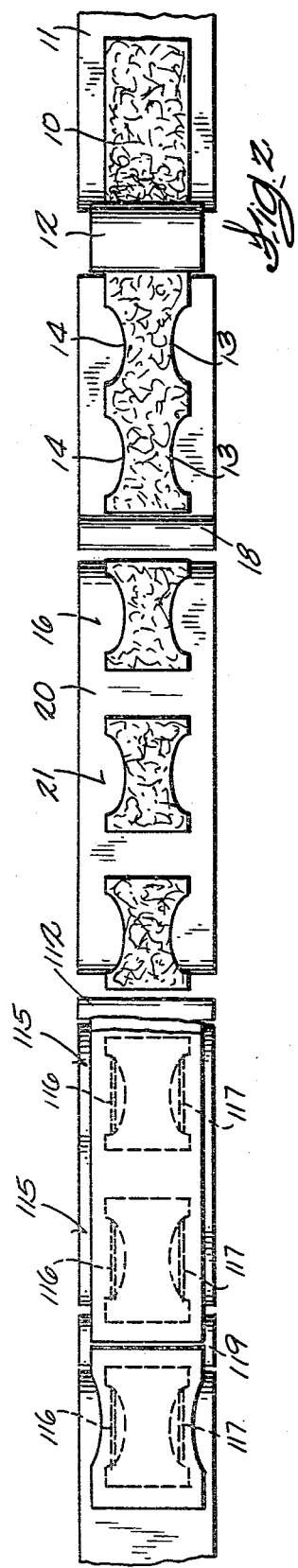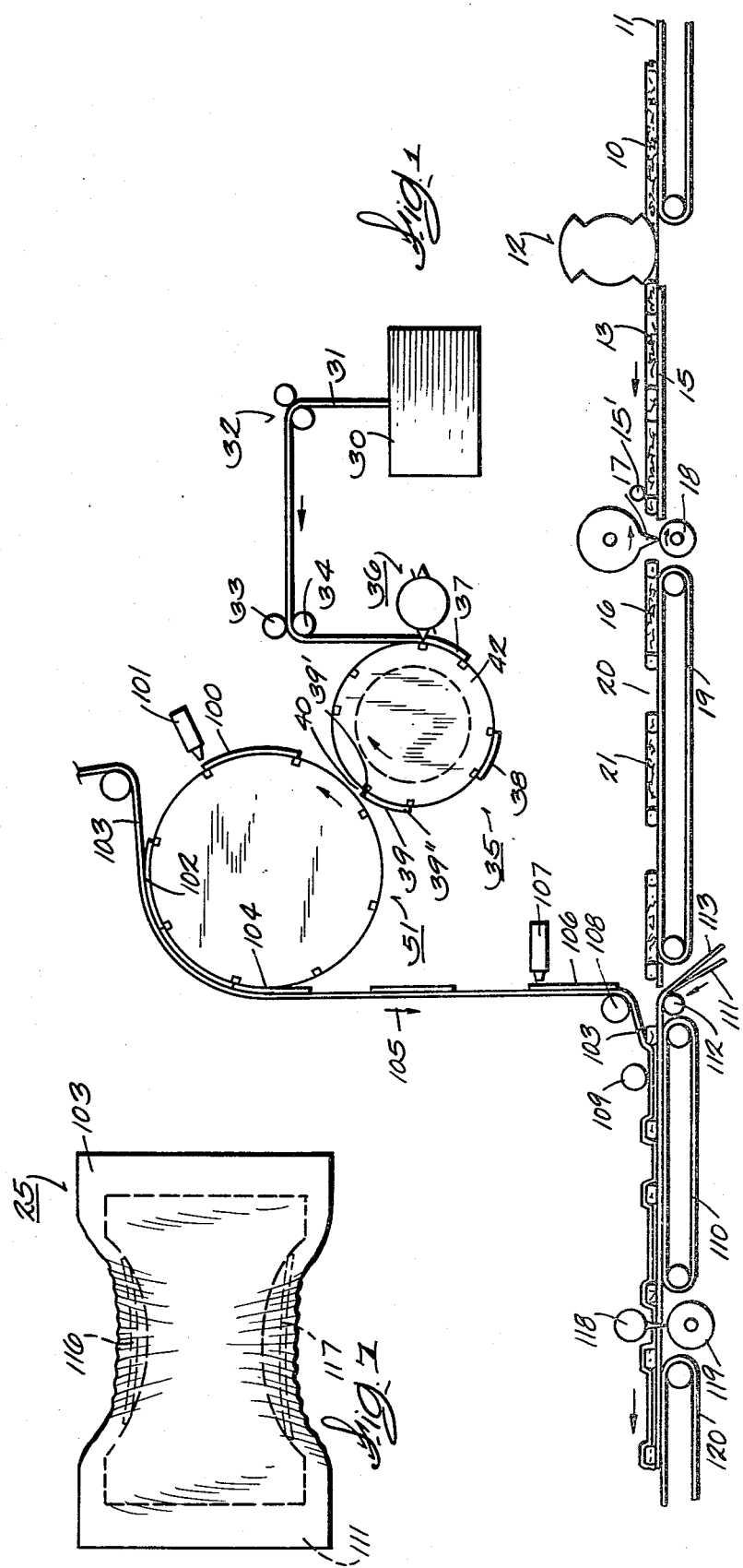

APPARATUS FOR APPLYING ELASTIC RIBBON SEGMENTS TO DIAPERS

This application is a continuation of application Ser. No. 180,256, filed Aug. 22, 1980 now abandoned.

This invention pertains to apparatus and a method of applying elastic ribbons in marginal regions of articles such as disposable diapers so they will conform to the contours of the portion of the body to which they are applied and thereby prevent leakage of body exudants collected by the diaper.

The new apparatus and method will be illustrated in connection with making disposable diapers but may be used to make other articles worn on the body as well. Basically, disposable diapers are composed of a fluid impervious film or backing sheet of a material such as polyethylene on which a fluid absorbent filler material or pad is adhered. Sometimes there is a porous fluid distributing sheet intervening between the impervious sheet and filler pad. Customarily, another porous sheet, commonly known as non-woven web is superimposed over the pad and has its margins adhered to the underlying flexible impervious backing sheet or the porous sheet which is adhered to it adjacent the edges of the pad. In some cases the pad and possibly the over and underlying sheets are notched on opposite sides to assist in having the sides of the diaper conform to contour of an infant's legs for improving sealing. It is also common practice to have a prestretched rubber ribbon running lengthwise of the notched region to enhance sealing about the infant's legs.

One scheme for installing the elastic ribbons in a continuous moving diaper web, which is ultimately severed to produce individual diapers is illustrated in U.S. Pat. No. 4,081,301. In general, this patent teaches feeding a moisture impervious backing sheet and a moisture pervious body interfacing top sheet simultaneously between a pair of substantially tangentially arranged rolls which are suitably contoured for allowing the absorbent filler pad to be inserted between and to pass along with the continuous moving sheets. Continuous elastic ribbons are also fed in parallel between the rolls to establish them between the backing sheet and top sheet of the diaper along the sides of each pad. Prior to entry between the rolls, the elastic ribbons are run over a series of metering rollers which cause the ribbons to be stretched before they enter between the rolls on which the superimposed backing and top sheets are fed. Adhesive is applied to the stretched ribbons periodically before they pass between the sheets and rolls. The stretched elastic ribbons run along the whole length of each diaper and across the gap between diapers in the continuous web. The adhesive sets quickly. In due course, a transverse cut is made through the overlaid top sheet and backing sheet to separate the moving web into individual diapers. The ribbon contracts and ruffles the leg interfacing edges of the diaper and the ribbon can be restretched when the diaper is filled about the leg and crotch regions of an infant. When the ribbon is cut, its opposite end portions to which no adhesive has been applied are free to snap into the interface between the top and backing sheets where the loose unadhered end portions perform no useful function. Hence, it is evident that a significant part of the ribbon is waste.

SUMMARY OF THE INVENTION

The apparatus and method disclosed herein is distinguished by the fact that it allows substantially all of the elastic ribbon to be functional to produce the desired contractile force for sealing around an infant's legs when the diaper is applied. Waste of ribbon is eliminated.

A further distinguishing feature of the apparatus and method disclosed herein is that it allows for easy maintenance of proper tension in the elastic ribbon without requiring sophisticated metering devices.

To outline the apparatus and method briefly, they involve applying and temporarily securing unstretched pairs of segments of an elastic ribbon successively to a first transport device which has a tangential component of motion at a first constant velocity. When the leading end of a segment arrives at a point adjacent a second transport device, that has a tangential component of motion at a second constant velocity which is higher than the first velocity, the leading end of the unstretched ribbon segment is engaged with the higher velocity second transport device at said point while the trailing end of the segment remains secured to the first transport device. The difference in the linear travel distances and velocities of the two devices results in the elastic ribbon segments being stretched. Next, the trailing end of the stretched elastic segment is released from the first device and engaged with the second device so that the segment may be transported in stretched condition. In a preferred embodiment, hot-melt, quick-setting adhesive is then applied as a thin line or series of dots over the length of the segments in each parallel pair as they move on the second transport device. Then one of the sheets, such as the fluid pervious top sheet comprising the diaper, is run over the adhesive coated side of the segments to adhere a pair of laterally spaced apart segments to the sheet. The adhesive sets by the time the sheet departs from the second transport device to take the segments along with it. Then as the successive segments advance on the sheet which is being conveyed under tension, a thin line or series of dots of adhesive is applied to the segments or to the sheet. The continuous tensioned sheet is then fed between a pair of rolls which also feed a continuous tensioned impervious backing sheet for the diaper on which other sheet the absorbent filler pad is being transported. Upon passing through these rolls, the edges of the top and back sheets, to the latter of which thin parallel lines of adhesive have been applied, become adhered. Later, the continuous web thereby formed is cut transversely at regular intervals at a distance from the ends of the elastic segment to produce the individual diapers. The adhered ribbon segments can then contract the sheets along the margins which interface with an infant's legs.

The method may also be used to install elastic bands at the margins of a diaper or the like which fit against the waist of a body.

How the foregoing and other more specific objects of the invention are achieved will be evident in the description of an illustrative embodiment of the invention which will now be set forth in reference to the drawings.

DESCRIPTION OF THE DRAWINGS

FIG. 1 is a primarily diagrammatic side elevation view of the parts of a diaper making machine which are necessary to describe the invention;

FIG. 2 is a plan view of the diaper web which is being transported through the machine in FIG. 1;

FIG. 7 is a plan view of a finished diaper as viewed from its body contacting side.

DESCRIPTION OF A PREFERRED EMBODIMENT

Figure 3:
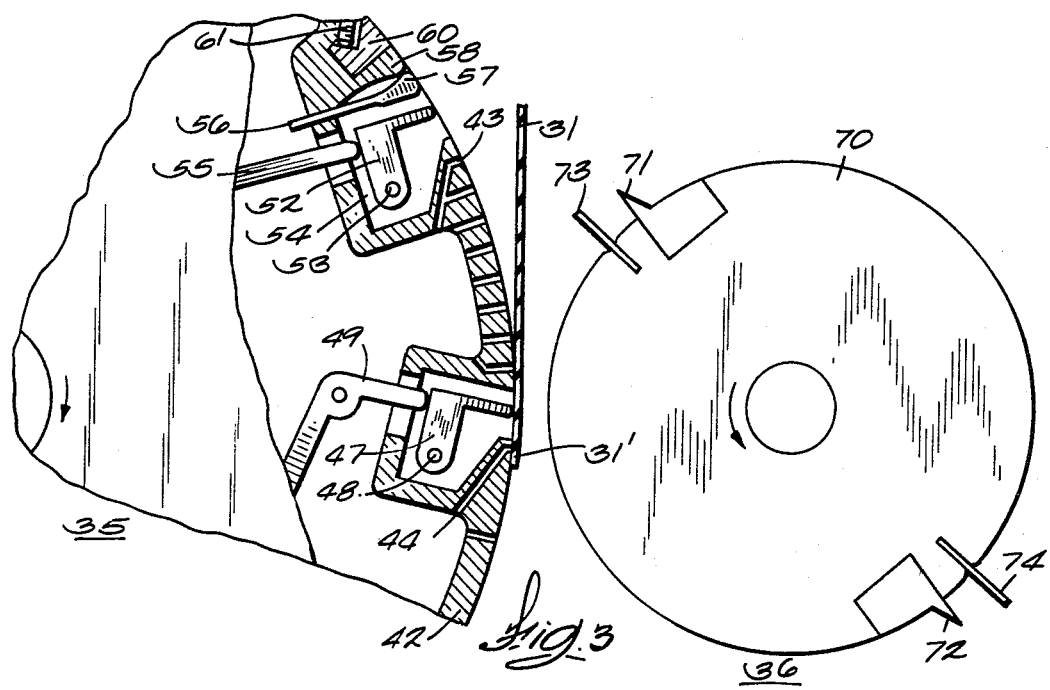
FIG. 3 shows a ribbon segment cut-off and tucking roll and a portion of a first transport device in the form of a ribbon segment transfer roll with parts broken away to show one phase of its operating sequence.

FIG. 1 shows those parts of a diaper making machine which are material to describing the new elastic ribbon applying apparatus and method. FIG. 2 shows a plan view of the conveyor on which the diaper web is formed. The first step in the diaper making process is to deposit a continuous layer of filler material 10 on a moving conveyor belt 11. In one type of diaper, this material is a mat of fine cellulosic fibers, sometimes called fluff, which has good fluid absorbent properties. By means of a rotating cutter 12, notches such as those marked 13 and 14 are cut out of mat 10 with regular periodicity. These notches are for allowing finished diapers to conform to the contours of the legs of the infant to which the diaper is applied.

As the filler advances on a plate 15 under the influence of a pull roll 15', it encounters another rotary cutter blade 17, see FIG. 1, which separates the mat into individual absorbent pads such as the one which is designated generally by the numeral 16. Cutter blade 17 acts against a rotary anvil 18. After the mat is cut into individual pads 16, these pads are transferred to another conveyor belt 19 which translates more rapidly than conveyor belt 11 so that a space 20 is created between consecutive individual absorbent diaper pads as exemplified by the pads marked 16 and 21. The suction devices for disposing of portions of the mat which are cut away to define the side notches and spaces between the individual pads are not shown but will be understood to be present by those skilled in the art.

As previously stated, a finished diaper such as the one marked 25 in FIG. 7 is comprised of a flexible fluid-impervious backing sheet of a material such as polyethylene and a fluid-pervious body interfacing porous top sheet of a material which is commonly known as nonwoven sheet. Typical absorbent pads 16 are interposed between these top and backing sheets and, in accordance with the invention, fully functional segments of elastic ribbon are installed between the sheets adjacent the filler pad notches, such as those marked 13 and 14 in FIG. 2, so that the diaper will be held in conformation with the contours of an infant's body. The manner in which the elastic segments are inserted will now be described.

In FIG. 1, a quantity of continuous elastic ribbon is stored in a box 30. The uncut ribbon being withdrawn from the box is marked 31. By way of example and not limitation, this ribbon is typically about one-fourth of an inch wide and about 0.017 of an inch thick. The ribbon runs through a straightener symbolized by rollers 32 in this schematic representation and the ribbon is withdrawn from box 30 by a pair of driven pinch rollers 33 and 34 which have their peripheries coated with a material such as silicone rubber for enhancing frictional engagement with ribbon 31.

The unstretched elastic ribbon is delivered to a first rotary ribbon segment transport device which is generally designated by the reference numeral 35 and is basically a vacuum roll with angularly spaced apart pairs of segment grippers and ejectors or lifters as will be described in detail shortly. The elastic ribbon is cut into segments with a synchronously rotatable cutter and tucker assembly which is generally designated by the numeral 36 in FIG. 1 and is shown in more detail in FIGS. 3 and 4. Spaced apart unstretched segments of the ribbon such as those marked 37, 38 and 39 in FIG. 1 are transported by vacuum roll 35 to a point 40 where the leading end 39' of a typical segment such as the one marked 39 is engaged by a suitable device on a second rotary transport device which is generally designated by the numeral 51 and which rotates faster than rotary device 35. Before discussing the segment transfer and stretching operation which results from cooperation of transport devices 35 and 51, the details of transport device 35 and associated cutter and tucker assembly 36 will be examined in reference to FIGS. 1, 3 and 4.

First rotary transport device 35 in the illustrated embodiment is basically a closed ended vacuum drum 42 which, as can be seen in FIG. 3, has a plurality of circumferentially spaced apart suction holes, such as those marked 43 and 44 in its peripheral wall for attracting and holding a portion of elastic ribbon 31 against its surface. Of course, there are two arrays of suction holes axially spaced apart on the periphery of vacuum roll 42 since a pair of elastic ribbon segments are to be installed between the fluid pervious front sheet and the fluid impervious backing sheet of the diaper within the notched areas 13 and 14 at each side of the diaper pad so there are in reality two ribbons fed in, only the one marked 31 being shown. For convenience, the first rotary transport device 35 which is based on vacuum drum 42 will be called a transfer roll 42 because ribbon segment transferring is its function. The term roll is used herein in its broadest sense to connote what is truly a cylindrical roll and other rotary transport devices such as a rotary conveyor, not shown.

Figure 4:
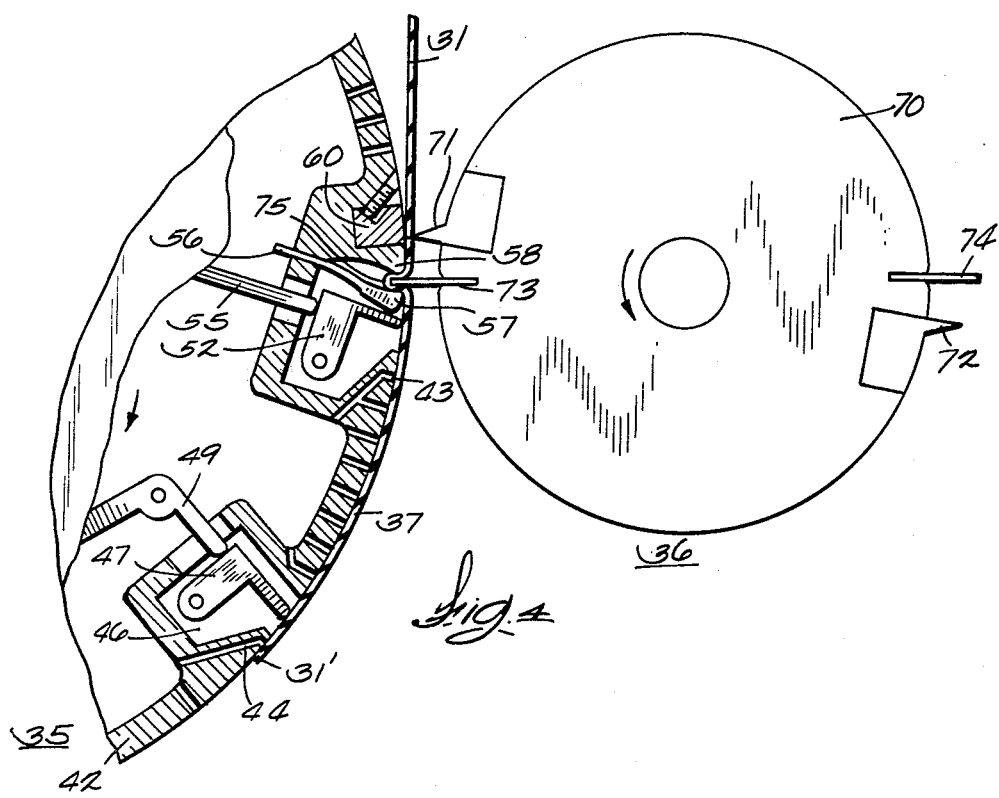
FIG. 4 shows parts similar to FIG. 3 but in another operational phase.

In FIG. 4, roll 42 is seen to include a cavity 46 in which ribbon lifter or ejector 47 is mounted for pivoting on a pin 48. Ejector 47 is biased for rotating counterclockwise as it appears in FIG. 3 by means of a spring which is not shown. Ejector 47 is actuated periodically by a properly timed cam 49 for lifting the leading end 31' of the elastic ribbon by a slight amount from the periphery of transfer roll 42 in connection with initiating transfer of the ribbon segment from transfer roll 42 in FIG. 1 to secondary rotary transport device or applicator roll 51 as it is otherwise called. In FIG. 3, there is another spring biased ejector or ribbon lifter 52 mounted on a pivot 53 in a cavity 54. Ribbon lifter 52 is actuated by an appropriately timed cam 55 in connection with releasing the trailing end 39" of a ribbon segment from transfer roll 42 and for engaging it with applicator roll 51. Cavity 54 also has a flat spring element 56 which has a pointed tip 57 which presses against an edge 58 of the cavity 54. A cutter anvil 60 is fixed in the periphery of roll 42 with set screws 61.

Next to transfer roll 42 there is a rotating power driven cutter and tucker device 36 as shown in detail in FIG. 3. This device comprises a cylinder 70 in which there are a pair of cutter blades 71 and 72. There are tucker fingers 73 and 74 projecting radially from cylinder 70 next to cutter blades 71 and 72, respectively. In operation, the interior of roll 42 is maintained at slightly below atmospheric pressure for creating suction through holes 43–44 for holding ribbon segments to the peripheral surface of the roll under the influence of atmospheric pressure.

The incoming continuous ribbon 31 has not been cut to form a segment in FIG. 3 but it is undergoing cutting in FIG. 4 where the oppositely rotating transfer roll 42 and cutter cylinder 70 are shown rotationally advanced or in a different phase relationship than in FIG. 3. In FIG. 4, the leading end 31' of the elastic ribbon is being attracted to the peripheral surface of transfer roll 42 by the negative pressure applied through vacuum hole 44. The major part of the segment length is also being attracted and secured on the roll 42 by other vacuum holes between those marked 43 and 44. Cutter blade 71 is acting against anvil 66 to shear off a segment of the elastic ribbon. Just prior to ribbon 31 being cut in FIG. 4, tucker finger 73 tucks a small loop of ribbon 75 in between the tip 57 of spring 56 and cavity edge 58. As properly synchronized rotation of the roll 42 and cutter cylinder 70 continues, the newly formed unstretched elastic ribbon segment 37 will be carried around rotationally and eventually reach the angular position of the ribbon segment marked 39 in FIG. 1. By way of example, and not limitation, in a practical application the elastic ribbon segments are about 4.5 to 5.0 inches long before they are stretched and they are finally stretched to about 9 to 10 inches when they are ultimately adhered to the diaper web.

Figure 5:
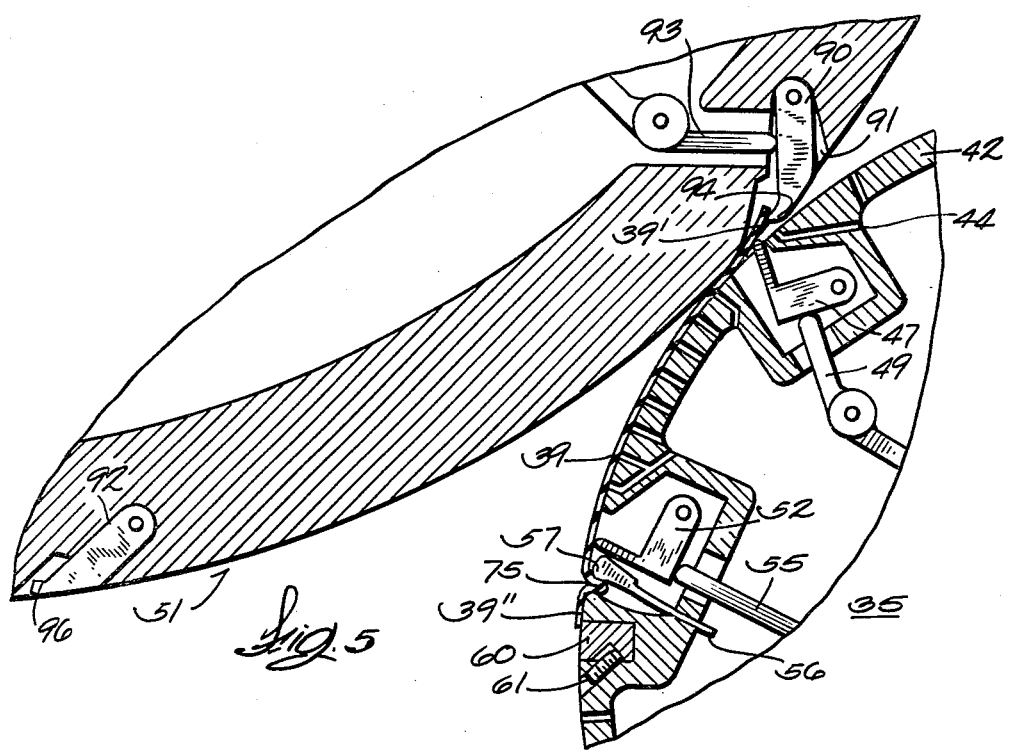
FIG. 5 depicts a fragment of the formerly mentioned transfer roll which is contiguous with a second transport device in the form of a fragmentarily shown applicator roll where these parts are in one operational phase.

In FIG. 5, one of the elastic ribbon segments 39 has been rotated by means of transfer roll 42 to the angular position where transfer of segment 39 to the second transport device in the form of applicator roll 51 is beginning. Applicator roll 51 rotates at the same angular velocity as transfer roll 42 but since the radius of applicator roll 51 is greater than the radius of transfer roll 42, the linear component of the velocity vector tangential to the surface of applicator roll 51 is greater than the corresponding linear component of transfer roll 42. The two rolls 51 and 42 are almost tangent as can be seen in FIG. 5. It will be evident that if the leading end 39' of segment 39 is grasped from the higher peripheral velocity applicator roll 51 while the trailing end 39" of the segment 39 is retained temporarily on the lower peripheral velocity transfer roll, the segment 39 must necessarily stretch. The amount of stretch corresponds with the ratio of the peripheral linear velocity components of the two rolls and to the ratio of their radii since they are driven at the same angular rate. In one design where each elastic ribbon segment is stretched to about twice its original length, from 4.5 to 9.0 inches by way of example, the periphery of the applicator roll 51 moves about 18.0 inches per diaper and the periphery of transfer roll 35 moves about 9.0 inches but, of course, these dimensions will vary in accordance with the size of the diapers.

In FIG. 5, leading end 39' of segment 39 has just been lifted away from the periphery of transfer roll 42. The body of segment 39 is being secured to the periphery of roll 42 primarily under the influence of vacuum within the roll and by the force of spring edge 57. The segment cannot fall off inadvertently. Cam 49 is acting on finger 47 to lift leading end 39'. A spring biased gripper finger 90 is pivotally mounted in a groove 91 in applicator roll 51. There are pairs of such angularly separated fingers distributed around the periphery of applicator roll 51. There is a pair for each segment position, in this case, four positions, on applicator roll 51. Gripper 92 shown in FIG. 5 is one that will eventually engage the trailing end 39" of segment 39 to secure the segment to the applicator roll in a stretched condition. In FIG. 5, leading gripper 90 is deflected at the moment by a cam 93 which has pressed the tip 94 of the gripper in a direction which results in formation of a gap into which leading end 39' of the elastic segment 39 may enter. A moment later in the joint rotation of the rolls 51 and 42, the force of cam 93 is removed from the gripper and its pointed tip 94 will squeeze the leading end 39'. Stretching of the segment 59 begins at that moment because of the peripheral velocity difference of the rolls.

Figure 6:
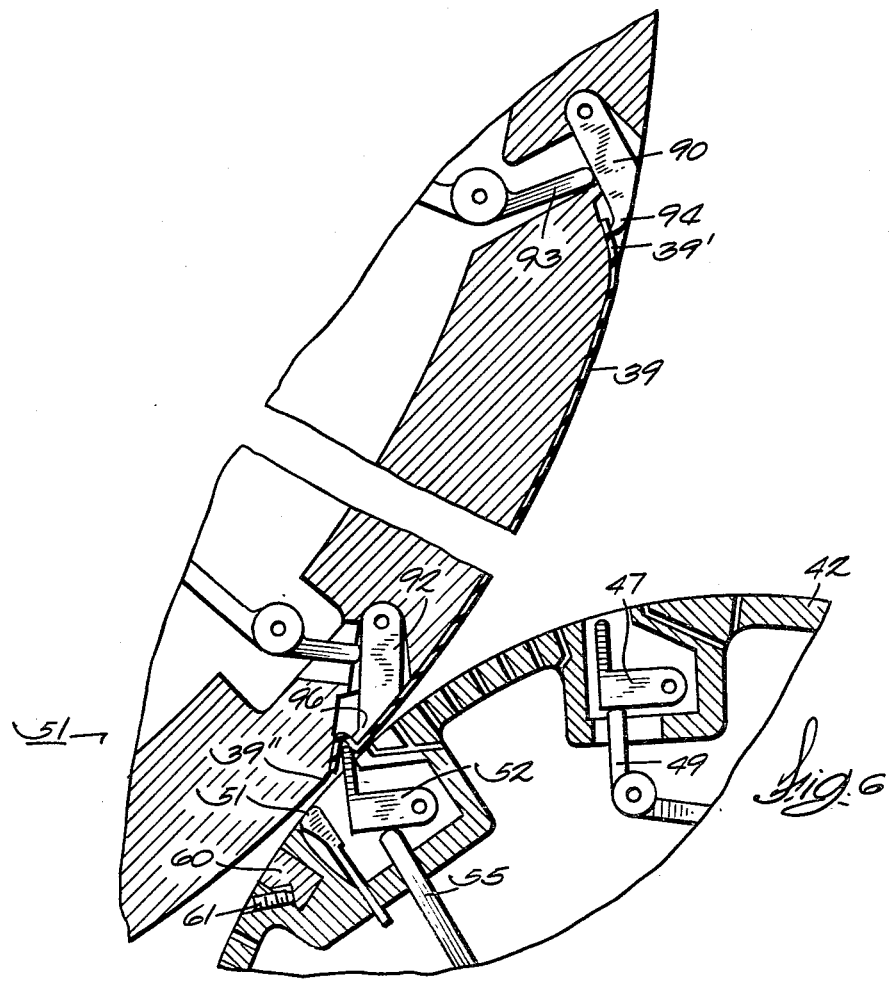
FIG. 6 shows the same parts as FIG. 5 in another operational phase.

In FIG. 6, roll 51, which has the higher tangential linear velocity at its periphery, has caused elastic segment 39 to attain a full stretched condition at which time it is necessary to release the trailing end 39" of segment 39 from transfer roll 42 and to have gripper 92 on the applicator roll 51 engage the elastic segment. Thus, cam 55 is operative at this time to actuate lift finger 52 which then releases the trailing end from spring finger tip 57. At this time, tip 96 of applicator roll gripper 92 squeezes the ribbon segment so that the later will be transported in a circular path on the applicator roll in a fully stretched condition. The loop where the lift finger 92 acts on the elastic segment in the vicinity of gripper finger tip 96 is exaggerated in size in the drawing because it was necessary to exaggerate the thickness of the segment for it to be readily visible. In reality, this loop is very small. Only a very small gripper compressive force is required to retain the stretched elastic ribbon segment on the applicator roll. In other words, the force on the tips 94 and 96 of the gripper fingers can be trivial.

Referring to FIG. 1, one may see that each stretched segment, such as the one marked 100, is carried past a glue applicator 101 which coats the outside surface of typical segment 100 with hot melt glue which sets quickly and is not stiff when it sets. Such glues are well-known to those involved in diaper manufacture. There is another glue applicator, not shown, behind applicator 101 for applying glue to another parallel running segment at the far side of the roll. Another segment 102 in FIG. 1 has advanced rotationally to a zone where it interfaces with a tensioned moving continuous porous and fluid-pervious sheet 103 which ultimately becomes the top or body interfacing sheet of the diaper. By the time segment 102 gets to the place where stretched segment 104 is presently located, firm adhesion has been obtained between the segment and porous or non-woven material sheet 103.

Porous sheet 103 advances in the direction indicated by the arrow marked 105 and stretched and adhered segments such as the one marked 106 pass another glue applicator 107 which coats the exposed sides of the two linearly aligned and laterally spaced apart segments which are deposited near opposite edges of sheet 103. Of course, there are segments running in parallel with each other on the transfer and applicator rolls although only one line is visible in the drawings. The sheet continues under a roller 108 after which it is pressed downwardly by another roller 109. Since the stretched elastic segments now have hot melt adhesive on them, they adhere to the tensioned fluid-impervious backing sheet which is running along the top surface of a conveyor belt 110. The notched absorbent pads of filler material such as the one marked 21 in FIG. 1 are delivered by conveyor belt 10 to conveyor belt 110 and superimposed on the moisture-impervious backing sheet 111 which is being fed over a roller 112 and runs along the surface of conveyor belt 110. Optionally, another porous sheet 113 for diffusing fluid interiorly of the diaper may be inserted as is done in some diaper designs. It is inserted herein to illustrate that fact. If porous sheet 113 is used, longitudinally extending fine stripes of glue will have been applied between sheets 111 and 113 to adhere the porous sheet to the fluid impervious sheet 111. Parallel stripes of glue will also, in this arrangement, be applied to the top surface of sheet 113 so it will adhere to the absorbent pad and to the top sheet 103. If only impervious backing sheet 111 is used, the glue stripes will be deposited on it. In any event, the adhesive bearing stretched elastic ribbon segments will adhere to the flexible impervious backing sheet if it is used alone in line with the notched regions of the absorbent pad. In FIG. 2, a typical diaper 115 which is still in the continuous web, illustrates how one set of stretched elastic ribbons 116 and 117 are disposed.

As the diapers in the still continuous web proceed along conveyor 110 they encounter a rotary cutter 118 in FIG. 1 which acts on a rotary anvil 119 to make a transverse cut through the top sheet 103 and backing sheet 111 to separate the web into individual diapers such as the one depicted in FIG. 7. It should be observed that the transverse cuts of the web are made remotely from the ends of the elastic segments so the segments are not cut and are fully functional in providing elasticity where it is most desirable. When the web is cut, the diaper contracts in the crotch region under the influence of elastic ribbons such as 116 and 117 in FIG. 7 which shows a completed diaper 25. The completed diapers are usually folded and stacked for being packaged with machinery which is not shown but is well-known.

In the illustrated embodiment, segment transport, stretching and application is implemented with two rolls 35 and 51 which have different peripheral velocities. It will be appreciated by those skilled in the art, however, that the segment cutoff, transfer stretch, glue and adhere sequence can be implemented by other mechanisms such as relatively moving rotary conveyors, not shown, equipped with appropriate gripping devices. Moreover, although a method and apparatus have been demonstrated in connection with applying elastic ribbon segments along the crotch interfacing regions of diapers, it should be evident to those skilled in the diaper making that apparatus based on the same principles could be used to apply elastic ribbon along the waist engaging edges of diapers too.

Although a preferred embodiment of the invention has been described in considerable detail, such description is intended to be illustrative rather than limiting, for the invention may be variously embodied and its true scope is to be determined only by interpretation of the claims which follow.

I claim:

1. A method of fixing elastic ribbon segments between interfacing nominally inelastic flexible sheets comprising an article such as a diaper in which it is desired to develop elasticity in at least one direction for inducing at least a portion of the article to conform to the contour of a body portion when the article is applied to a body, said method including the steps of:

releasably securing unstretched segments of said elastic ribbon successively to a first transport device moving at a first velocity for the leading end of the segment to arrive at a place adjacent a second transport device moving at a second velocity which is higher than said first velocity, engaging the leading end of the segment with the higher velocity second transport device at said place while the trailing end remains secured to the first lower velocity transport device such that said elastic ribbon segment will be stretched, engaging the trailing end of the stretched elastic segment with said second transport device and substantially simultaneously releasing said trailing end from the first transport device for said stretched segment to be transported solely on said second device in stretched condition, causing a moving one of the flexible sheets of which said article is comprised and a stretched elastic segment being transported to come into contact relationship after a selected one or the other of said segment or sheet has had adhesive applied for adhering said stretched segment and sheet together, then running said first sheet in contact with a moving second one of said sheets comprising the article for adhering said sheets together where one or the other of said segment or said sheet has had adhesive applied, and cutting said sheets transversely remotely from the ends of the stretched segments to yield individual flexible articles and enable said stretched segments to contract the regions of said articles to which they are applied.

2. A method of fixing segments of elastic ribbon in regions of diapers which are to be elastic for conforming margins of the diapers to the contour of the body where the diapers are composed of at least two nominally inelastic flexible sheets having an absorbent material between them, said method including the steps of:

securing unstretched segments of elastic ribbon which have leading and trailing ends successively to a first rotating roll having a first peripheral velocity for the leading ends of the segments, respectively, to arrive at a place adjacent a second rotating roll having a second peripheral velocity which is higher than said first velocity, engaging the leading end of each segment with said higher velocity second roll at said place while the trailing end of the segment remains secured to said first lower velocity roll such that the ribbon segment will be stretched, then substantially simultaneously releasing the trailing end of the segment from the first roll and engaging said trailing end with the second roll for said segment to be carried by said second roll in stretched condition, causing a tensioned moving one of said flexible sheets of which said diaper is comprised and a segment on the second roll to come into contact after one or the other of said sheet or segment has had adhesive applied to it for adhering the stretched segment to the sheet, applying adhesive to the stretched segments as they advance with the sheet, next putting said sheet with said segments on it in contact with another of said flexible sheets while successive ones of said absorbent pads are interposed between said sheets, and cutting said sheets transversely remotely from the ends of said segments to yield individual diapers and enable the stretched segments to contract the regions of said diapers to which the segments are applied.

3. Apparatus for fixing segments of elastic ribbon between interfacing nominally inelastic flexible sheets having absorbent filler material between them to compose an article such as a diaper in which it is desired to develop elasticity in at least one direction for inducing at least a portion of the article to conform to the contour of the body when the article is applied to a body, said apparatus comprising:

a first roll means for rotating with a predetermined peripheral velocity and second roll means adjacent said first roll means for rotating with a peripheral velocity greater than that of the first roll means, means on said first roll means for releasably securing individual segments of unstretched elastic ribbon which have leading and trailing ends and have been deposited on said first roll means in succession as said roll means rotates, means on said second higher velocity roll means for gripping the leading end of each segment in the succession while the trailing end of the segment remains secured on said first lower velocity roll means to thereby cause said segment to be stretched, means on said first roll means for releasing the trailing end of said segment when it has been stretched a predetermined amount and means on said second roll means for engaging said trailing end such that said segment is transported on said second roll means in stretched condition, means for placing a moving one of said sheets which comprises a continuous web of said articles in contact with successive stretched segments moving on said second roll means, means for applying quick setting adhesive between said segments and sheet before contact is made such that as said one sheet and segment move together said adhesive will set and adhere said segment in stretched condition to said sheet, means for applying adhesive to the successive stretched segments on said one moving sheet when said sheet separates from said second roll means, means for moving another of said sheets which comprises said article and has adhesive thereon in interfacing relation with said one sheet and means for inserting a succession of absorbent filler materials between said sheets to produce a continuous web of said articles, and means for cutting said web transversely at regular intervals at a place remote from the ends of the stretched elastic segments.

4. The apparatus as in claim 3 wherein said means for applying adhesive before contact is made with said one sheet is located adjacent the path followed by each stretched segment as it rotates on said second roll means for applying adhesive to the segments.

5. Apparatus for fixing segments of elastic ribbon between interfacing nominally inelastic flexible sheets having absorbent filler material between them to compose an article such as a diaper in which it is desired to develop elasticity in at least one direction for inducing at least a portion of the article to conform to the contour of the body when the article is applied to a body, said apparatus comprising:

a first roll means for rotating with a predetermined peripheral velocity and second roll means adjacent said first roll means for rotating with a peripheral velocity greater than that of the first roll means, said first roll means having a plurality of cutter anvils disposed in circumferentially spaced apart relationship about its periphery each of which anvils has a sequence of elements preceding it in the direction of roll rotation including and in the order of a gripper for the trailing end of an unstretched elastic ribbon segment, first lifter means and lifter operating means for releasing said trailing end from said gripper, a series of holes for enabling vacuum to be developed on said periphery, said second lifter means and lifter operating means for lifting the leading end of the ribbon segment from said roll means, a movable device supporting a cutter blade and a tucker element adjacent the blade, said device being adjacent said first roll means and being movable synchronously therewith, means for disposing the leading end of a continuous ribbon over said second lifter means for an ensuing portion of said ribbon to be attracted to said periphery of said first roll means to position said ribbon for said tucker to tuck it in said gripper and for said cutter blade to cut said ribbon against said anvil and thereby produce a segment with said leading and trailing ends for being carried in unstretched condition on said first roll means, a movable device supporting a cutter blade and a tucker element adjacent the blade, said device being adjacent said first roll means and being movable synchronously therewith, means for disposing the leading end of a continuous ribbon over said second lifter means for an ensuing portion of said ribbon to be attracted to said periphery of said first roll means to position said ribbon for said tucker to tuck it in said gripper and for said cutter blade to cut said ribbon against said anvil and thereby produce a segment with said leading and trailing ends for being carried in unstretched condition on said first roll means, said second roll means having circumferentially spaced apart cooperating leading and trailing grippers disposed in its periphery and means for actuating said grippers in synchronism with operation of said lifters, the phase relationship of said roll means being such that said second lifter on said first roll means lifts said leading end of the ribbon segment for being gripped by the leading gripper on said higher velocity second roll means to thereby stretch said segment and said first lifter on said first roll means lifts said trailing end of said segment for being gripped by the trailing gripper on said second roll means to thereby hold said segment in stretch condition on the second roll means, means for placing a moving one of said sheets which comprises a continuous web of said articles in contact with successive stretched segments moving on said second roll means, means for applying quick setting adhesive between said segments and sheet before contact is made such that as said one sheet and segment move together said adhesive will set and adhere said segment in stretched condition to said sheet, means for applying adhesive to the successive stretched segments on said one moving sheet when said sheet separates from said second roll means, means for moving another of said sheets which comprises said article and has adhesive thereon in interfacing relation with said one sheet and means for inserting a succession of absorbent filler materials between said sheets to produce a continuous web of said articles, and means for cutting said web transversely at regular intervals at a place remote from the ends of the stretched elastic segments.

6. A method of fixing elastic ribbon between two interfacing nominally inelastic flexible sheets comprising an article such as a diaper in which it is desired to develop elasticity in at least one direction for inducing at least a portion of the article to conform to the contour of a body portion when the article is applied to a body, in which the ribbon is adhesively united in a stretched condition between the two flexible sheets as the sheets are advanced in a tensioned condition and the sheets are severed at intervals in a direction transverse to their direction of advance to yield individual flexible articles including the steps of:

(a) cutting the ribbon in the unstretched condition to produce segments of ribbon of predetermined length, (b) releasably securing the unstretched segments of said elastic ribbon successively to a first transport device moving at a first velocity for the leading end of the segment to arrive at a place adjacent a second transport device moving at a second velocity which is higher than said first velocity, (c) engaging the leading end of the segment with the higher velocity second transport device at said place while the trailing end remains secured to the first lower velocity transport device such that said elastic ribbon segment will be stretched, (d) engaging the trailing end of the stretched segment with said second transport device and substantially simultaneously releasing said trailing end from the first transport device for said stretched segment to be transported solely on said second device in stretched condition, (e) applying an adhesive to at least one of the advancing flexible sheets and the stretched segments and bringing the stretched segments on said second transport device into interfacing engagement with said one advancing flexible sheet to adhesively unite the stretched segments to the sheet, (f) adhesively uniting the spaced stretched segments with the other of the advancing flexible sheets, and (g) severing the sheets transversely of their direction of advance between the spaced segments.

7. A method according to claim 6 wherein the spaced stretched segments are adhesively united with the other of the advancing flexible sheets by applying an adhesive to at least one of the spaced stretched segments and the other flexible sheet and contacting the other flexible sheet with the stretched segments carried on the one advancing flexible sheet, and successively interposing absorbent pads between the two advancing flexible sheets as the stretched segments are brought into contact with the other flexible sheets.

8. Apparatus for fixing elastic ribbon between two interfacing nominally inelastic flexible sheets comprising an article such as a diaper in which it is desired to develop elasticity in at least one direction for inducing at least a portion of the article to conform to the contour of a body portion when the article is applied to a body, the apparatus comprising:

means for advancing the flexible sheets in a tensioned condition, means for cutting the ribbon in the unstretched condition to produce segments of ribbon of predetermined length, first and second transport devices, means operable releasably to secure the unstretched segments of said elastic ribbon to said first transport device moving at a first velocity to transport the leading end of the segment to a place adjacent said second transport device moving at a second velocity higher than said first velocity, means operable to engage said leading end of the segment with the higher velocity transport device at said place while the trailing end remains secured to the first lower velocity transport device such that said elastic ribbon segment will be stretched, means for engaging the trailing end of the stretched elastic segment with the second transport device and substantially simultaneously releasing said trailing end from the first transport device for the stretched segment to be transported solely on said second device in a stretched condition, said means for advancing the flexible sheets being arranged to advance one flexible sheet into interfacing engagement with the stretched segment transported on the second transport device, means operable to apply an adhesive to at least one of the one flexible sheet and the stretched segments before an interfacing engagement between the segments and the one sheet, means operable to apply an adhesive to at least one of the other flexible sheet and the stretched segment already on the one sheet, and means for interposing absorbent pads successively between the two advancing flexible sheets as the stretched segments on the one sheet are brought into contact with and for adhering to said other flexible sheet.

9. Apparatus according to claim 8 wherein the first transport device comprises a first roll means arranged to rotate with a predetermined peripheral velocity, the second transport device comprises a second roll means adjacent to the first roll means and arranged to rotate with a peripheral velocity greater than that of the first roll means.

* * * * *